United States Patent [19]
Sikorski et al.

[11] Patent Number: 5,834,445
[45] Date of Patent: Nov. 10, 1998

[54] PROCESS FOR PREPARING DECOLORIZED CAROTENOID-CYCLODEXTRIN COMPLEXES

[76] Inventors: Christopher Sikorski, 1805 Davis St., Whiting, Ind. 46394; Joel L. Schwartz, 5225 Pooks Hill, Promenade Apt. 315 South, Bethesda, Md. 20814; Gerald Shklar, 7 Chauncy La., Cambridge, Mass. 02138

[21] Appl. No.: 552,374

[22] Filed: Nov. 3, 1995

Related U.S. Application Data

[63] Continuation-in-part of Ser. No. 339,018, Nov. 14, 1994, abandoned, which is a continuation-in-part of Ser. No. 947,067, Sep. 18, 1992, abandoned, which is a continuation of Ser. No. 741,203, Jul. 30, 1991, abandoned, which is a continuation of Ser. No. 469,171, Jan. 24, 1990, abandoned, and a continuation-in-part of Ser. No. 392,857, Aug. 11, 1989, abandoned, said Ser. No. 947,067, Sep. 18, 1992, abandoned, is a continuation-in-part of Ser. No. 860,201, Mar. 26, 1992, abandoned, which is a continuation of Ser. No. 708,130, May 29, 1991, abandoned.

[51] Int. Cl.⁶ .................. A61K 31/715; A61K 31/07; A61K 31/015
[52] U.S. Cl. .................. 514/458; 514/725; 514/763
[58] Field of Search .................. 514/58, 458, 562, 514/725, 763

[56] References Cited

U.S. PATENT DOCUMENTS

| | | |
|---|---|---|
| 2,827,452 | 3/1958 | Schlenk et al. . |
| 4,416,901 | 11/1983 | Bochskandl . |
| 4,713,398 | 12/1987 | Nonomura . |
| 4,732,759 | 3/1988 | Shibanai et al. . |
| 4,870,060 | 9/1989 | Müller . |
| 4,915,965 | 4/1990 | Tanaka . |
| 4,927,850 | 5/1990 | Bayless et al. . |
| 4,985,455 | 1/1991 | Motono . |
| 5,024,998 | 6/1991 | Bodor . |
| 5,300,508 | 4/1994 | Valla et al. . |

FOREIGN PATENT DOCUMENTS

| | | |
|---|---|---|
| 5788123 | 6/1982 | Japan . |
| 61-212322 | 9/1986 | Japan . |
| 62-267261 | 11/1987 | Japan . |
| 63-83021 | 4/1988 | Japan . |
| 4244059 | 9/1992 | Japan . |
| 625156 | 2/1994 | Japan . |
| 8200251 | 2/1982 | WIPO . |

*Primary Examiner*—Raymond Henley, III
*Attorney, Agent, or Firm*—Trask, Britt & Rossa

[57] ABSTRACT

Complexes of β carotene with cyclodextrin are described, having reduced color intensity and a shift of color to tones more neutral than the deep red of uncomplexed β carotene. When these complexes are added to topical compositions such as typical skin cream bases in amounts up to 1.0% β carotene w/v, the result is a cream having a pinkish to beige color which is cosmetically acceptable, as opposed to the mustard orange to red color seen in creams containing like amounts of uncomplexed β carotene.

18 Claims, 2 Drawing Sheets

Fig. 2

PROCESS FOR PREPARING DECOLORIZED CAROTENOID-CYCLODEXTRIN COMPLEXES

RELATED APPLICATION

This application is a continuation-in-part of application Ser. No. 08/339,018, filed Nov. 14, 1994, now abandoned which is a continuation-in-part of Ser. No. 07/947,067 filed Sep. 18, 1992 now abandoned, which in turn is a continuation of Ser. No. 07/741,203, filed Jul. 30, 1991, now abandoned, and which is a continuation of Ser. No. 07/469,171, filed Jan. 24, 1990, now abandoned, and a continuation-in-part of, Ser. No. 07/392,857 filed Aug. 11, 1989 now abandoned. Ser. No. 07/947,067 filed Sep. 18, 1992, now abandoned is also a continuation-in-part of Ser. No. 07/860,201, filed Mar. 26, 1992 now abandoned, which is a continuation of Ser. No. 07/708,130 filed May 29, 1991 now abandoned.

BACKGROUND OF THE INVENTION

1. Field of the Invention

The invention relates to generally to complexes of carotenoid anti-oxidants with cyclodextrins, and especially to carotenoid-cyclodextrin complexes having properties of reduced red color intensity in combination with topical cream or paste carriers.

2. State of the Art

Carotenoids including β carotene have been shown to be effective as inhibitors of the development of at least some kinds of tumors induced by environmental mutagens (see for example Suda, Schwartz and Shklar, "Inhibition of experimental oral carcinogenesis by topical beta carotene," *Carcinogenesis* 8:711–715, 1986; J. S. Bertram et al., "Diverse carotenoids protect against chemically induced neoplastic transformation", *Carcinogenesis* 11:671–678, 1991; G. Shklar et al., "Regression of experimental cancer by oral administration of combined α tocopherol-β carotene", *Nutrition and Cancer* 12:321–325, 1989; Toma et al., "In vitro effects of β carotene on human oral keratinocytes from precancerous lesions and squamous carcinoma", *Anti.Cancer. Drugs* 2:581–589, 1991). In the Suda et al. study, topical application of a 2.5% β-carotene solution in mineral oil to a 7,12-dimethylbenz[a]anthracene (DMBA) induced squamous cell carcinoma reduced the number and sizes of tumors occurring on the buccal pouch of a group of hamsters. Beta carotene has also been shown to inhibit human oral cancer cells in vitro and to preferentially kill tumor cells over normal (non-tumor) cells ("Selective cytotoxic effects of carotenoids and α tocopherol on human cell lines in vitro, J. Schwartz and G. Shklar, *J. Oral and Maxillofacial Surg.* 50:367–373, 1992). In at least some cases, β carotene appears to be superior to Vitamin A in its tumor inhibitory effects (Schwartz and Antoniades, "Suppression of oral carcinoma cell growth with enhanced expression of hsp 70 and wild type p53 following treatment with β carotene or retinyl palmitate", manuscript submitted, 1993).

Vitamin E (alpha tocopherol) has also been shown to inhibit the development of carcinogen-induced epidermoid carcinomas, and in some cases to completely prevent their growth. A combination of beta carotene and alpha tocopherol administered orally was found to be synergistic in its ability to inhibit the development of cancer. Tocopherols and carotenoids are among the agents known to act as anti-oxidants and/or to combat the deleterious effects on skin of excess exposure to sunlight.

In the skin, excess exposure to sunlight and/or oxidizing agents may appear as wrinkling and drying. An article by Pugliese, *Cosmetics and Toiletries*, Vol. 102, April 1987, pages 19 through 44, (hereby incorporated by reference) discusses the undesirable effects on the skin of oxidants including and/or stemming from free radicals. The article further notes that systemic treatment with antioxidants may be ineffective for the skin if the antioxidant levels achieved are not appropriate. A further difficulty of oral administration for antioxidant treatment of the skin is that skin has limited storage for some antioxidants. Also, in individuals with poor circulation the active substances such as vitamins, vitamin-related compounds, or other anti-oxidants may not be carried in sufficient quantities to the affected skin. Older people and/or chronic smokers are especially prone to experience poor circulation, particularly in limbs and extremities. Poor circulation in itself may lead to various kinds of skin damage such as thinning skin, carcinomas, skin chaffing and cracking, and the like.

Development of skin cancer in humans is strongly correlated with exposure of the skin to carcinogens, particularly to ultraviolet light in the sun's rays. Many individuals who have spent large periods of time working and/or recreating outdoors, are subject to the development of benign and malignant skin tumors. Some must return frequently to a doctor to have benign and/or slow-growing skin tumors removed, while others suffer serious illness or die as a result of such malignancies as melanoma. Persons whose skin is exposed to carcinogenic chemicals, of which crop insecticides, defoliants, and photographic chemicals are but a few examples, may also be at a higher risk for the development of skin or other kinds of tumors.

There are furthermore individuals suffering from mild or severe genetic conditions which enhance the sensitivity of the skin to sunlight and chemicals. Such individuals are at significantly greater risk for short-term effects such as sunlight-induced skin burning and chapping, as well as long-term effects such as skin tumors and premature aging and wrinkling of the skin.

Numerous articles discussing the use of vitamin A, vitamin E and B-carotene individually in various manners such as dietary treatment, injection and topical application are referenced and briefly described on the Suda et al. article, the contents of that article being incorporated herein by reference. Oral ingestion of vitamin compositions, including some such as vitamins A and E and pro-vitamin A (beta carotene) which can function as antioxidants, has been shown in some cases to be effective for treating or preventing disease conditions, including pre-cancerous and cancerous conditions. However, systemic use of vitamins is not always effective, possibly because the anti-oxidant does not reach the target organ (the skin) in sufficient concentrations.

Various retinoids closely related to Vitamin A, have been put into skin creams, as well as mixtures of retinoids and other agents such as a tocopherol. Skin creams with retinoids have been used to treat acne, and claims have been made that retinoid creams can reverse aging changes in skin and remove wrinkles. However, retinoids are toxic, teratogenic and cancer-promoting.

In contrast, beta carotene and alpha tocopherol are non-toxic or demonstrate toxicity so low as to be negligible. Combinations of β carotene and alpha tocopherol may be particularly desirable; it has been shown that sequential topical application of these compounds to mucosa stimulate Langerhans cells and thus enhance local immune response.

It is thus highly desirable to provide a topical formulation containing β carotene, and further desirable that the formulation include vitamin E and/or other anti-oxidants. A host of skin lotions and creams are available which contain Vitamin A (a substantially colorless compound), but applicants presently are not aware of any commercial over-the-counter skin preparations containing β carotene in significant concentrations. Instead, β carotene is usually marketed in the form of dry tablets or food-supplements for oral ingestion.

One reason for the low apparent commercialization of topical compositions and creams containing β carotene may be the unacceptable color, etc, to the consumer of creams in which β carotene is not well-solublized. β carotene and other carotenoids are compounds having a strong red or orange to brown color. Previous attempts by applicants to include β carotene in a skin cream have produced a cream with an unpleasant mustard-like appearance, which can stain the skin and clothing or other objects with which it comes into contact. Furthermore, the lack of water solubility may also interfere with passage through the skin.

The class of compounds generally known as cyclodextrins comprises cyclic oligosaccharides having 6, 7, or 8 glucopyranose units, arranged in a relatively rigid circular structure. Some cyclodextrins are naturally occurring compounds, however these are not generally soluble in water. Cyclodextrins modified at the 2, 3, and 6 hydroxyl sites have a greatly enhanced solubility in water. U.S. Pat. Nos. 4,870,060 to Muller (issued Sep. 26, 1989), 5,024,998 to Bodor (issued Jun. 18, 1991) and 4,727,064 to Pitha (issued Feb. 23, 1988) describe cyclodextrins particularly useful for their solubilizing properties. Some of these compounds may be dissolved in water to concentrations of 50% w/v or more.

Cyclodextrins are known for solubilizing drugs and other compounds, including some vitamins, for oral or parenteral administration (see for example U.S. Pat. No. 4,533,637 to Mikio et al, issued Aug. 6, 1985) and Japanese Patents Nos. 63083021, 2,108,622 and 6,009,062 (published Apr. 13, 1988; Apr. 20, 1990; and May 27, 1985, respectively).

However, so far as applicants are aware, it was not previously known that mixing β carotene with a cyclodextrin would produce a complex which was partially or entirely decolorized in comparison to uncomplexed β carotene. Nor to applicants knowledge was it recognized that such reduced color intensity would enable the provision of cosmetically acceptable topical compositions containing β carotene, such as skin creams and tooth pastes.

Thus, a need remains for a topical composition providing carotenoids and especially β carotene in an easily applied, cosmetically acceptable form, at an effective concentration. There is further a need for such a composition which will be readily absorbed either topically or by the gastrointestinal system.

SUMMARY

The invention comprises a carotenoid-cyclodextrin complex (abbreviated CC complex) whose color intensity is significantly reduced, and the hue significantly neutralized, as compared to the uncomplexed carotenoid. The preferred carotenoid is β carotene. In a preferred embodiment, the reduction in color intensity and hue are sufficient that a cream containing β carotene of between 0.3% and 1% by weight in a typical skin cream base formulation, has a pale pinkish or beige color which is cosmetically acceptable, as opposed to the orange to mustard color of such a cream containing the same amount of uncomplexed β carotene is added. Presently preferred embodiments comprise complexes of β carotene with β cyclodextrin, and creams prepared with the β carotene/ β cyclodextrin complexes.

The invention further encompasses a skin cream comprising a hydrophilic base cream and a cyclodextrin-carotenoid complex in an amount to provide from about 0.1 percent to about 1.0 percent carotenoid by weight of the skin cream, and having a reduced color as compared to a cream of identical composition except for the omission of the cyclodextrin (e.g., containing the same amount of β carotene added in pure form as opposed to being complexed with cyclodextrin).

Optionally, additional solubilizing means, such as a solubilizing agent selected from the group comprising methylene chloride, 1,2-dimethoxyethane, dimethylsulfoxide, and tetrahydrofuran, may be combined with the β carotene to facilitate preparation of the complex, or with the C—C complex prior to its addition to the cream. The solvent may or may not be eliminated from the complex before its addition to a cream. Also, to further stabilize the β carotene in the complex and in the finished cream, the C—C complex may be incorporated into liposomes or microsomes as known in the art.

Desirably, the skin cream further includes one or more additional anti-oxidant compounds, such as Vitamin E, glutathione, and superoxide dismutase. Preferably, the total quantity of antioxidants in the skin cream, including β carotene, is from at least about 4 percent by weight up to about 10.0 percent by weight.

BRIEF DESCRIPTION OF THE DRAWINGS

The file of this patent contains at least one drawing executed in color. Copies this patent with color drawing(s) will be provided by the Patent and Trademark Office upon request and payment of necessary fee.

In the drawings:

FIG. 2 is a table of COLOR-AID swatches selected as approximate matches for various powder complexes of the invention and for creams incorporating them.

DETAILED DESCRIPTION OF THE ILLUSTRATED EMBODIMENTS

Figure 1:
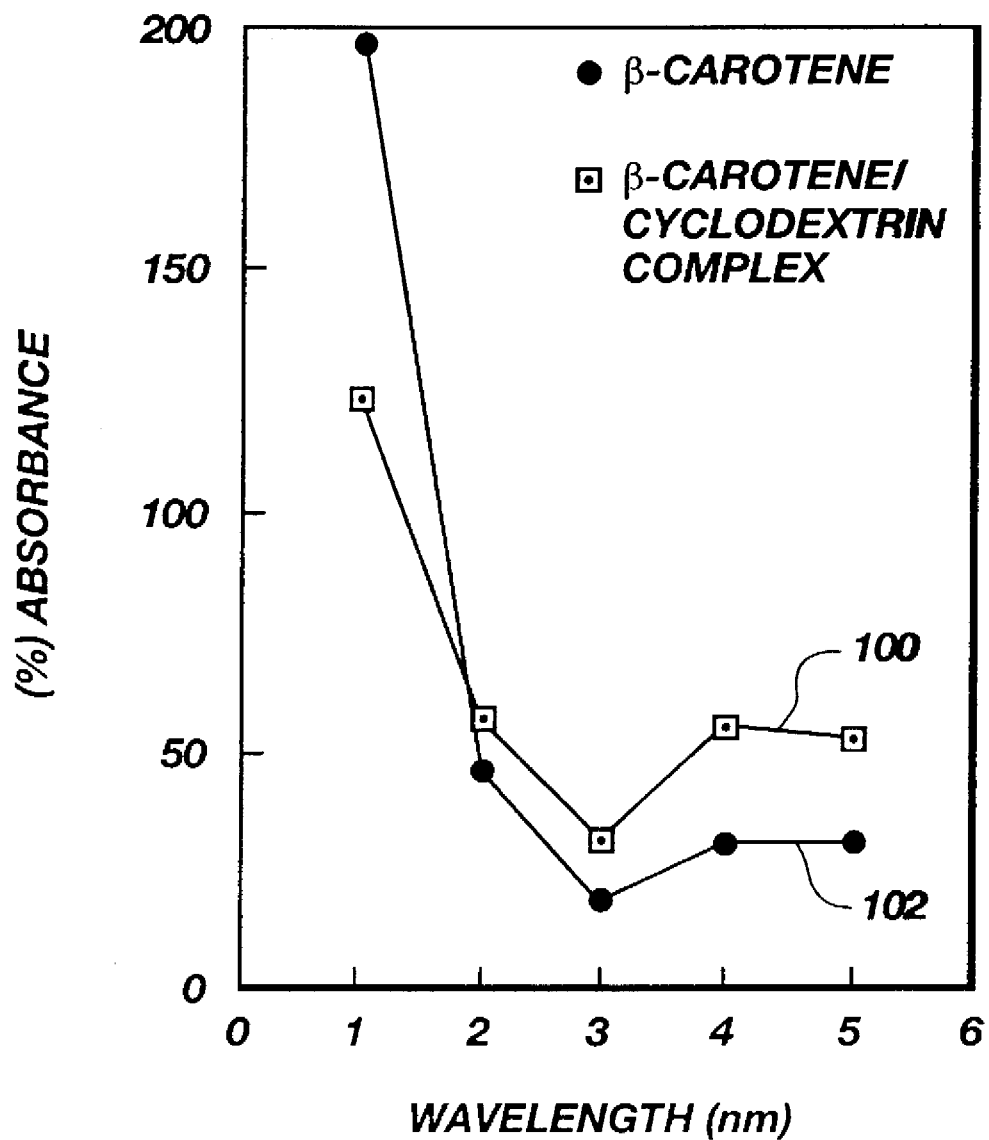
FIG. 1 is a chart depicting the absorbance of a lipid-oil suspension containing uncomplexed vs. complexed β carotene.

The presently preferred embodiments of the complex are prepared by mixing a solution of β carotene in an organic solvent such as methylene chloride, with an aqueous solution of a cyclodextrin. The mixture is stirred overnight, and the precipitate is separated by filtration and dried. The dried precipitate is the complex.

To determine the percent loading of the products, a spectrophotometric analysis is performed. Approximately 10 mg (milligrams) of complex is mixed with 5 ml (milliliters) of water and 5 ml of methylene chloride in a tube which is sealed against evaporation. This mixture is incubated in a 60° C. waterbath for about an hour, with occasional agitation. The mixture is then allowed to cool at room temperature without agitation, until the phases were sufficiently separated. The absorbance at 450 nm of the methylene chloride fraction is measured spectrophotoetrically, and compared to a standard curve obtained by preparing solutions of varying concentrations of β carotene in methylene chloride. Generally, a useful standard curve includes measurements of known β carotene concentrations over the range from about 0.001 mg/ml to about 0.01 mg/ml. The amount of active β carotene in the complex is expressed as a percent loading, where percent loading=[grams β carotene/grams complex]×100%). The value of percent loading as thus calculated is related to the relative molecular weights of β carotene to cyclodextrin; a product having one β carotene complexed per cyclodextrin molecule would have a percent loading of about 30% to 40%, depending on the particular cyclodextrin used.

EXAMPLE 1

Complex #1 (0.1M β-CD/0.1M β carotene)

An 800 ml aqueous solution containing 100 grams (0.0881 moles) of beta-cyclodextrin (β-CD) was prepared by stirring in a light-shielded flask. To this solution was added 47.3 grams (0.0881 moles) of beta-carotene in 50 ml methylene chloride, and the resulting mixture was stirred overnight under vacuum at room temperature. Filtration of the red colored suspension yielded a red precipitate, which was collected and oven dried under vacuum at 60° C. for 6 hrs to yield 130 grams of dry product. The product was found to have a 32.3 percent loading.

EXAMPLE 2

Complex #2 (0.11M β-CD/0.053M β carotene)

An aqueous solution of 200 grams (0.1762 moles) of beta-cyclodextrin in 1600 ml of water was prepared. The solution was stirred as in the previous examples, and 50 ml of methylene chloride containing 47.3 grams (0.0881 moles) of β carotene was added. The mixture was then stirred overnight at ambient temperature under a vacuum. The resulting red colored suspension was filtered and the red precipitate collected and oven dried under vacuum at 60° C. for 6 hrs, yielding 239 grams of dry product with 10.6 percent loading.

EXAMPLE 3

Complex #3 (0.10 M β-CD/0.034 M β carotene)

Sixteen hundred ml of an aqueous solution containing 190 grams (0.1674 moles) of beta-cyclodextrin (β-CD) was prepared. The solution was stirred in a flask covered with aluminum foil to protect from light. Fifty ml of methylene chloride with 30 grams (0.0559 moles) of beta-carotene dissolved therein was added to the solution, and the mixture was stirred overnight at room temperature under a vacuum. The resulting red colored suspension was filtered and the red precipitate collected and oven dried under vacuum at 60° C. for 6 hrs. The product weight recovered was 197 grams, and the percent loading was 6.5%.

EXAMPLE 4

Complex #4 (0.16M τ-CD/0.16M β carotene)

Eight hundred seventy-five ml of an aqueous solution containing 200 grams (0.1542 moles) of τ-cyclodextrin (τ-CD) was prepared. The solution was stirred in a dark environment and 83 grams (0.1542 moles) of β carotene in 100 ml methylene chloride was added. The mixture was stirred overnight at ambient temperature under a vacuum. The resulting red suspension was filtered and a red precipitate was collected and oven dried under vacuum at 60° C. for 6 hrs. The dried product weighed 170 grams and was found to have 20.0 percent loading.

EXAMPLE 5

Complex #5 (0.16M τ-CD/0.08M β carotene)

An aqueous solution of 57.1 grams (0.0440 moles) of τ-CD in 250 ml water was prepared and stirred in a flask covered with aluminum foil to protect it from light. Twenty-five ml of methylene chloride containing 11.8 grams (0.0220 moles) of β carotene in 25 ml methylene chloride was added. The mixture was stirred overnight at ambient temperature under a vacuum. The resulting red colored suspension was filtered and the red precipitate was collected and oven dried under vacuum at 60° C. for 6 hrs. The weight of dry product recovered was 35 grams, with the percent loading being 24.3%.

EXAMPLE 6

Complex #6 (0.166M τ-CD/0.055M β carotene)

Seven hundred and fifty milliliters (ml) of an aqueous solution containing 171.4 grams (0.1321 moles) of gamma-cyclodextrin (τ-CD) was prepared. The solution was stirred and the flask was covered with aluminum foil to protect from light. To this solution a mixture of β-carotene (23.6 grams; 0.0440 moles) in 50 ml methylene chloride was added. The mixture was allowed to stir overnight at room temperature under a vacuum. The resulting red colored suspension was filtered and the red precipitate was collected and oven dried under vacuum at 60° C. for 6 hrs. The dry weight of the precipitate was 105 grams. The percent loading of complex was determined to be 10.0%.

EXAMPLE 7

Complex #7 (0.04M Ac-β-CD/0.023M β carotene)

An aqueous solution of 75.2 grams (0.0373 moles) of acetylated β-cyclodextrin (Ac-β-CD) in 800 ml water was prepared. The mixture was stirred in a dark environment as above, and 10 grams (0.0186 moles) of β carotene in 100 ml methylene chloride was added. The mixture was stirred overnight at ambient temperature under a vacuum, after which the red colored suspension was filtered and the red precipitate collected and oven dried under vacuum at 60° C. for 6 hrs. Eighty-three grams of product with a 13.4 percent loading were obtained.

EXAMPLE 8

Complex #8 (0.039M OS-β-CD/0.02M β carotene)

A solution of 69 grams (0.0373 moles) of octenylsucci-nylated beta-cyclodextrin (OS-β-CD) in eight hundred ml of water was prepared and stirred as above. One hundred fifty ml of methylene chloride containing 10 grams (0.0186 moles) of β carotene was added to the mixture. The mixture was stirred under vacuum overnight at room temperature. The resulting red colored suspension was filtered and the red precipitate collected and oven dried under vacuum at 60° C. for 6 hrs. Seventy-five grams of dry product with 14.5 percent loading was recovered.

EXAMPLE 9

Complex #9 (0.04M Et-g-e-β-CD/0.02M β carotene)

A 400 ml aqueous solution containing 45.5 grams (0.0186 moles) of 2-ethylhexyl glycidyl ether β-cyclodextrin was prepared. The suspension was stirred as above and 10 grams (0.0093 moles) of β carotene in 50 ml methylene chloride was added. The mixture was stirred overnight at ambient temperature and under a vacuum. The result was a red-colored suspension which when filtered yielded a red precipitate. The precipitate was collected and oven dried under vacuum at 60° C. for 6 hrs, yielding a dry weight of 38 grams having 8.6 percent loading.

EXAMPLE 10

Complex #10

An aqueous solution containing 100 grams (0.1028 moles) of alpha cyclodextrin was prepared, to which 47.3 grams (0.1028 moles) of β carotene were added. The mixture was stirred overnight at room temperature, under a vacuum and protected from light. The resulting red suspension was filtered and the precipitate collected and oven dried under vacuum. The product had a dry weight of 95 grams and was found to have a 9.9% loading.

Complexes prepared with different types of cyclodextrin were observed to vary somewhat in hue or tone, as well as being paler in color than uncomplexed β carotene. Some degree of lightening of the product complex may be due to the loadings of less than 100%. That is, if the product had a 15% loading with β carotene, then it contains about 15 percent β carotene per unit weight, as opposed to pure β carotene powder, with the remaining 75% being cyclodextrin which in pure form (prior to complexation with β carotene) is white or ivory. In general, the α cyclodextrin/carotene complexes had a light purplish color, the β cyclodextrin/complexes had a light red color, and the powdered τ cyclodextrin/carotene complexes were light orange in color. Pure β carotene has a deep, red to orange-red color.

Preparation of creams containing β carotene/cyclodextrin complexes

Creams containing cyclodextrin-complexed β carotene and uncomplexed β carotene were prepared by adding the respective carotene preparation to one or more of several different commercially available creams. The commercial creams used include LUBRIDERM, NOXZEMA, POND'S hand cream, POND'S Cold Cream, and NIVEA moisturizing cream. The amount of complex needed to achieve a β carotene content of 1% by weight was calculated using the measurement of percent loading for the particular complex, and this amount was added to the cream as purchased. Control samples contained 1% uncomplexed β carotene by weight of the cream. In general, the creams prepared with α-CD/carotene complexes appeared pink or light blue-red (cool red) to purplish or mauve, those with β-CD/carotene complexes were light red (warm red), and those prepared with τ-CD/carotene complexes were red-orange to orange. The tones of the creams generally paralleled the tones of the complexes in powder form, but there were some exceptions depending upon type of cream. Since the amount of β carotene by weight is the same in all the cream samples, including those to which β carotene was added in pure form and those to which the β carotene was added in the form of β carotene/cyclodextrin complex, differences in color intensity and hue are not ascribable to a simple dilution effect.

Description of color by naming of the color is obviously highly subjective and variable. However, as known to those in the visual and decorative arts, there are several systems and standard terms for classifying color. In the Munsell system, color is classified according to hue, value (tints and shades), and saturation (also sometimes called intensity, brightness, or chroma) (A. Munsell, *A Color Notation*, Munsell Color Co., Baltimore, 1936). Hue refers to the basic perceived color, that is, red, orange, yellow, green, blue, etc. A complete set of hues in a standard color wheel generally consists of 12 hues, these being red, red-orange, orange, yellow-orange, yellow, yellow-green, green, blue-green, blue, blue-violet, violet, and red-violet. Saturation describes the overall vividness or intensity of a color. Value refers to the relative lightness or darkness of a color, with a "tint" being a color lightened by addition of white, and a "shade" being a color darkened by addition of black.

The COLOR-AID swatchbook and booklet (available from Color-Aid Corp., 37 East 18th Street, New York, N.Y.) are based on a classification system similar to the Munsell system, for use by artists, designers, etc, to classify and select or match colors. The swatchbook contains paper swatches of 314 different standardized colors, each coded according hue, tint, and shade. In addition to hue, tint, and shade, the COLOR-AID coding system uses the term "pastel" to refer to colors having varying amounts of both black and white. The color differences among complexed and uncomplexed β carotene and among creams containing complexed vs. uncomplexed β carotene are here characterized according to the COLOR-AID swatchbook.

The COLOR-AID codes comprise a sequence of letter and number codes separated by dashes. For each color, the code begins with a one or two letters representing one of the 12 standard hues, such as R for red, RO for red-orange, YO for yellow-orange, etc. The hue code is followed by a series of numbers and letters which indicate the level of tint (T1, T2, T3, T4 being increasing addition of white) and shade (S1, S2, S3, S4 being increasing addition of black). Alternatively, if the color is derived from a hue by addition of both black and white, the letter "P" meaning "pastel" follows the hue code letter, with P1, P2, P3 indicating increasing "grayness" or "dirtiness" of the tone. For the "P" tones, a third number code follows the P1, P2 or P3 designation, and indicates further addition of whiteness.

Thus, R-Hue indicates a particular red hue at its highest intensity or saturation, while R-T1 indicates the same red hue with whiteness added to a first level, and R-T2 indicates the red hue with whiteness added to a second level. That is, R-T1 is paler than R-Hue; in turn, R-T2 is paler than R-T1, R-T3 is paler than R-T2, and so on. RO-S1 indicates a red-orange hue, darkened by addition of one level of black. RO-P1—1 indicates a red-orange modified by a first level of added grayness, RO-P2-1 indicates the same red-orange modified by a second (increased) level of added grayness, and RO-P2—2 indicates the latter color further modified by addition of a level of whiteness. The coding system is more fully described in The New COLOR-AID Booklet, pub. 1990 by Color-Aid Corp., the contents of which are hereby incorporated by reference. It should be noted that while the selection of colors included in the swatchbook may change, the coding applied to a particular color as of the 1989 product, does not change.

For the most repeatable and accurate results, color matching should be performed in daylight or under daylight-spectrum lighting. Conventional fluorescent light and incandescent light are both known to distort the appearance of colored samples. Also, it is desirable that the color matching be performed against a white or light gray background. In the present case, color matching was performed under fluorescent lighting of the full-spectrum type.

Figure 2:
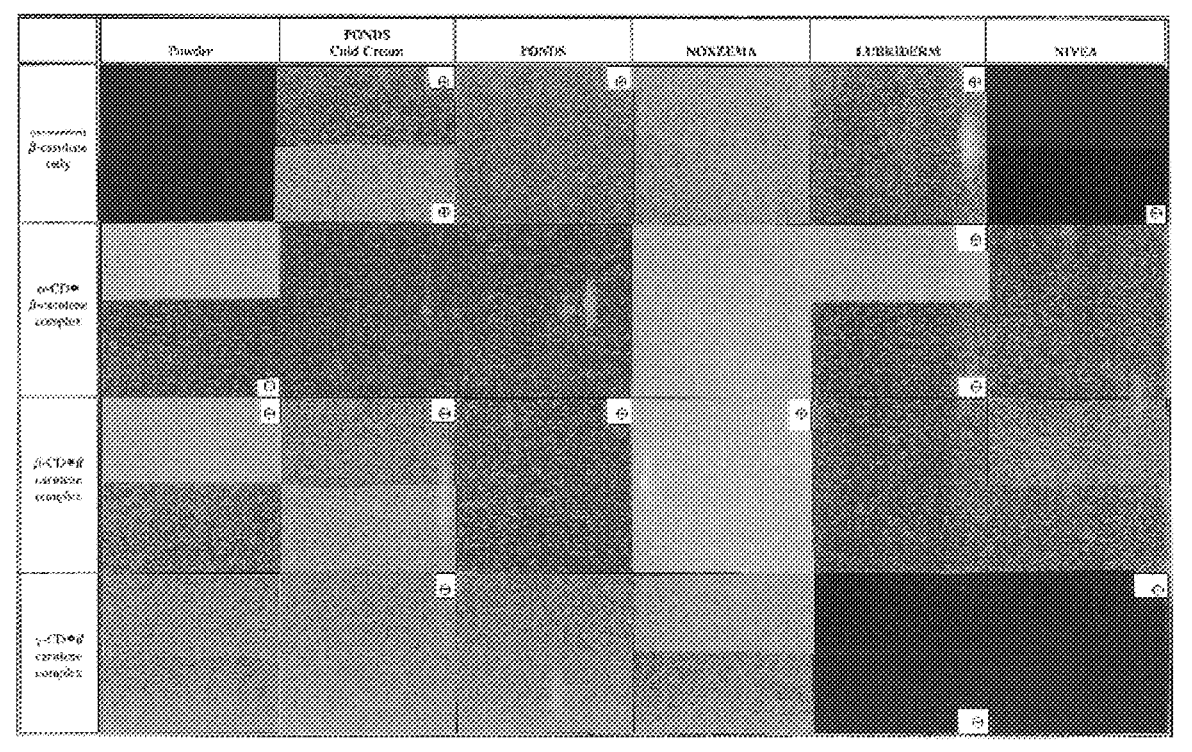

Table I lists the codes of swatches from a COLOR-AID swatchbook dated 1989, which most nearly match the color of each indicated composition, and FIG. 2 contains samples of the swatches themselves arranged in a table format similar to Table I. In cases where there did not appear to be an exact match among the COLOR-AID swatches, two swatch codes and swatch samples are presented, and the those of the corresponding swatches. Also, when the sample was distinctly darker than the nearest matching swatch, an encircled + sign is shown next to the code. Similarly, if the sample was distinctly paler than the nearest match, an encircled − sign is shown next to the code. All of the creams were white or ivory prior to addition of β carotene or β carotene-CD complex. The complexes used in the creams evaluated in Table I were prepared in substantially the same way as in Examples 1–10 above. The percent loading of the α cyclodextrin complex was 15%, that of the β cyclodextrin complex 12%, and that of the τ cyclodextrin complex about 25%.

with a computer colorant formulation system can reproduce the coded color, regardless of the materials or colorants involved.

Table II contains the COLORCURVE codes of COLOR-CURVE swatches matched to the same set of samples as in Table I. The greater selection of colors and values in the COLORCURVE swatches resulted in generally closer matches. In the COLORCURVE code, the first number specifies the level, that is, the value of the equivalent gray tone; the level numbers increase from darker values to lighter values. For example, Level 55 colors are paler than

TABLE I

|  | Powder | PONDS Cold Cream | PONDS | NOXZEMA | LUBRIDERM | NIVEA |
|---|---|---|---|---|---|---|
| β-carotene only |  | RO-P2-1⊕ |  |  |  | R-S1 |
|  | R-S1 | O-P2-1⊕ | O-S1⊕ | O-P2-1 | RO-P2-1⊕ | R-S2⊖ |
| α-CD ~ βcarotene complex | R-P3-2 |  |  |  | RO-P3-2⊕ Ro-P3-1⊖ |  |
|  | R-P2-1⊖ | YO-S2 | RO-P 2-1 | R-P3-2 | R-P3-2 | R-P2-1 |
| βCD ~ β carotene complex | R-P1-1⊖ | O-S1⊖ |  |  |  | RO-P2-1 R-P2-1 |
|  | RO-P2-1 | O-P2-1 | RO-P2-1⊖ | RO-P2-2⊕ | R-P2-1 O-S2 | R-P1-1⊕ |
| γ-CD ~ β carotene complex | O-S1 |  |  | O-P2-1 | RO-S2⊖ |  |
|  | RO-P2-1 | O-S1⊖ | O-S1 | RO-P2-1 | O-S1⊕ | RO-S2⊕ |

Actual color should be understood as being approximately intermediate between second system useful for characterizing the observed color changes is that marketed under the name COLORCURVE, by Colwell General, Inc., 200 Sixth Street, Fort Wayne, Ind. 46808. In the COLORCURVE system, colors are scaled on a 3-dimensional scheme. One dimension, which for convenience here will be termed the vertical dimension, is value, defined more or less according to Munsell (op cit). The two dimensions of each plane are hue and intensity or saturation. The "hues" of the COLOR-CURVE system are the four primary colors of visible light: red, yellow, green and blue. Like the COLOR-AID system, the COLORCURVE system provides coded swatches for color matching. Each coded color in the COLORCURVE system is defined by light reflectance values, tristimulus values, and L*a*b* values, these being colorimetric parameters known in the art. The colorimetric data for each code are found in the COLORCURVE Data Book, pub. 1989 by Colorcurve Systems Inc., Minneapolis, Minn., and also available from Colwell General Inc. Upon being provided with the reflectance and colorimetric data corresponding to a particular COLORCURVE coded color, any manufacturer Level 50 colors, which in turn are paler than Level 45 colors. The second and third codes each consist of a letter followed by a single-digit number. The letter identifies one of four hues (R-red, Y-yellow, B-blue, and G-green, these being the four "primary" colors in light), and the number describes the intensity of the hue. Thus, L40 R3 Y2 specifies value Level 40, red hue saturation level of 3, and yellow hue saturation level of 2 (where increasing numbers from 1 to 8 designate increasing saturation levels). For colors characterized by more than one hue (which includes all of the colors pertinent here), lower saturation levels correspond to more neutral colors, with the most neutral colors having combined saturation scores (the sum of the saturation level for both hues) of 2 to 4, with the most neutral colors having combined saturation scores of 2 to 3.

TABLE II

|  | Powder | A | B | C | D | E |
|---|---|---|---|---|---|---|
| β-carotene only | L40 R5Y4 | L50 R3YS L55 R3YS | L45 R4YS L45 R3Y4 | L55 R2Y4 | L50 R3Y4 | L45 R4Y3 L45 R3Y2 |
| α-CD ~ β-carotene complex | L60 R2Y2 L60 R1Y1 | L55 R2Y5 L60 R2Y5 | L55 R2Y4 L55 R2Y3 | L60 R1Y2 | L60 R1Y1 L60 R1Y2 L60 R2Y2 | L50 R2Y1 L50 R2Y2 |
| β-CD ~ β carotene complex | L60 R3Y3 L60 R2Y2 | L55 R3YS | L55 R3YS L55 R3Y4 | L60 R2Y3 L55 R2Y3 | L55 R2Y3 L50 R3Y3 | L50 R2Y3 L55 R3Y3 |
| γ-CD ~ β carotene complex | L50 R4YS L50 R3Y4 | L50 R3Y5 L50 R4Y5 | L45 R4YS | L55 R2Y4 | L45 R4Y5 | L45 R3Y4 |

As can be seen from Table II, most of the creams prepared with α-CD/carotene complexes and β-CD/carotene complexes had colors of value levels 55 to 65, whereas of the creams prepared with uncomplexed β carotene, most had colors of value levels 45 to 50. Additionally, most of the α-CD/carotene creams had red intensity levels between 1 and 3 and yellow intensity levels between 2 and 4, whereas most of the uncomplexed β carotene creams had red intensity levels ranging between 3 and 5 and yellow saturation levels of 4 to 5. The β-CD/carotene creams had red and yellow saturation levels more similar to the uncomplexed β carotene creams. The τ-CD/carotene creams appeared similar in value level and in hue/saturation levels, to those with uncomplexed β carotene.

A third, long-recognized system for matching and duplicating colors is the PANTONE Process Color Specifier. This system is based on the four-color printing process using magenta (M), cyan (C), yellow (Y), and black (K) inks. The PANTONE Specifier also includes swatches of colors varying in value and hue and identified by invariant codes. However, each code in the Process Color Specifier corresponds to the combination of the four above-identified standard printing colors with which the coded color can be reproduced. For example, for PANTONE code S103-5, the formula is C=20, M=50, Y=35, and K=25. Any printer using the four-color process will know how to use this formula to duplicate the color of the swatch coded S103-5. The four-color printing process has been almost universally used for color printing for many years, and the PANTONE Specifier is generally recognized as the industry standard for specifying printed colors. Table III shows the PANTONE codes for colors matching the same set of powder and cream samples for which COLOR-AID and COLORCURVE equivalents are given in Tables I and II.

TABLE III

| Powder | A | B | C | D | E | |
|---|---|---|---|---|---|---|
| β-carotene only | S89-2<br>S44-2 | S51-3<br>S45-2<br>S83-2 | S66-6<br>S39-4 | S52-4 | S65-5<br>S103-3 | S105-3<br>S100-5<br>S96-3 |
| α-CD ~ β-carotene complex | S79-7<br>S102-6<br>S103-2 | S39-3<br>S48-4<br>S47-4<br>S38-3 | S52-4<br>S39-4<br>S102-5 | S85-7 | S103-8<br>S85-7<br>S79-7<br>S102-6 | S105-5<br>S103-5<br>S103-6<br>S103-8 |
| β-CD ~ β carotene complex | S89-8<br>S79-7<br>S102-6 | S51-3<br>S83-2 | S51-3<br>S83-2<br>S63-5 | S63-6<br>S81-6<br>S102-5 | S79-6<br>S65-6 | S65-6<br>S79-6 |
| γ-CD ~ β carotene complex | S40-1<br>S65-5 | S44-2<br>S40-1 | S66-6<br>S45-2 | S52-4<br>S39-4 | S52-2<br>S59-3 | S66-5<br>S45-1 |

As evident from Tables I–III and FIG. 2, the composition of the skin cream may also influence the resulting color. This effect is observed in the controls (the samples to which uncomplexed β carotene was added), as well as in the test complex creams. For example, in the control samples, the deepest and most intense colors occurred in NIVEA Moisturizing Lotion, the most consistently pale and neutral tones were produced by the NOXZEMA Original cream and PONDS Cold Cream, and the LUBRIDERM lotion and PONDS hand cream were generally intermediate in intensity and color. Table IV is a comparison of the ingredients in each of the five creams, as given on the U.S. commercial labels thereon. For purposes of the comparison, however, the ingredients are not listed in the same order as on the labels.

The PONDS Cold Cream tended to shift the color of the powdered form towards a more yellow tone. The NIVEA Moisturizing cream generally caused the least shift in color from the powder, irrespective of whether the powder was pure β carotene or a CD/carotene complex. The NOXZEMA Original cream tended to reduce the intensity and shift the color of the carotene to a more neutral tone, regardless of whether the carotene was in complexed form. In general, it was observed that creams having mineral oil or petrolatum among the main lipid components by weight produced more deeply colored products, while those having vegetable oils such as linseed oil or soybean oil as the main lipid component produced the palest and most neutral-toned products. Also, the inclusion of glycerine in a cream appeared to intensify the color of the product.

At present, the α cyclodextrin complexes are preferred, as these provided the palest and/or most neutral tones when incorporated into a cream. The β cyclodextrin complexes, however, appear to be nearly as good as the α-CD complexes, whereas the τ cyclodextrin complexes appeared to be little better than the raw β carotene.

It has been observed that the β carotene content of the powdered complex, as measured spectrophotometrically, may decline somewhat during storage at room temperature even when shielded from light. This degradation or decrease in β carotene content is substantially inhibited by storage of the complex at low temperatures, preferably in a freezer and under nitrogen. However, once incorporated into one of the above creams, the β carotene is much more stable and the cream can be stored at room temperature without drastic decline in β carotene content.

Nevertheless, it is contemplated that to improve the shelf stability of creams and other compositions containing the β carotene/cyclodextrin complex, it may be desirable to incorporate the complex into liposomes or microsomes, prior to mixing it into the carrier. Alternatively, the complex could be prepared in a sealed ampoule, and mixed with the carrier by the user immediately prior to its use.

TABLE IV

| NDS<br>Cold Cream | PONDS<br>Skin Cream | NOXZEMA<br>Original | LUBRIDERM<br>Lotion | NIVEA<br>Moistur. Lotion |
|---|---|---|---|---|
| Mineral oil | Mineral oil | Linseed oil<br>Soybean oil | Mineral oil | Mineral oil |
| Water | Water<br>Petrolatum | Water | Water<br>Petrolatum | Water |
| Beeswax | Candelilla wax | | | Simethicone |
| | | | Lanolin<br>Lanolin alcohol | Lanolin alcohol |
| | Stearic acid | Stearic acid | Stearic acid | |
| | Glyceryl stearate | | | Glyceryl stearate |
| | Glycerin | Propylene glycol | | Glycerin |
| | Isopropyl palmitate | | | Isopropyl myristate |
| | Sorbitan oleate | | Sorbitol | |
| | Laureth-23 | | | |
| | Imidazolidinyl urea | Triethanolamine | Triethanolamine | |

TABLE IV-continued

| NDS Cold Cream | PONDS Skin Cream | NOXZEMA Original | LUBRIDERM Lotion | NIVEA Moistur. Lotion |
|---|---|---|---|---|
| | Cetyl alcohol | Gelatin | Cetyl alcohol | Cetearyl alcohol Hydroxypropyl methylcellulose |
| | Methylparaben Propylparaben | Butylparaben Methylparaben Propylparaben | | |
| NaBorate | Na$_3$EDTA | CaOH NH$_4$OH | NaCl | Sodium hydroxide |
| Ceresin Carbomer | Ceresin Carbomer | Carbomer Camphor Eucalyptus oil Clove oil Menthol Phenol | | Carbomer |
| | Tea | | | Chamomile extract Methylchioroiso- thiazolinone |
| | | | Methyliso- thiazolinone | |

It is generally thought that solubilization of hydrophobic compounds by cyclodextrins is mediated at least in part by complexing of the compound in the hydrophobic cavity in the ring. It is further believed that the ability to complex particular compounds depends in part on the relative "sizes" of the compound and the hydrophobic cavity. Thus, a cyclodextrin useful for solubilizing a particular compound or group of related compounds whose approximate molecular dimensions are known, may be selected to have a cavity similar in size or larger than the chosen compound(s).

At present, cyclodextrins having 7 glucopyranose units in the ring are preferred for the invention, as they provide a complexing cavity closer in size to the β carotene molecule than cyclodextrins having more or fewer glucopyranose units. However, other cyclodextrins may be more useful for carotenoid compounds which differ in size or shape from β carotene.

Among the carotenoid compounds to which the present invention may be extended are α carotene, canthaxanthin, and mixtures thereof which may also include β carotene. Beta carotene and alpha carotene are readily commercially available from Hoffman LaRoche and other sources. Canthaxanthin is available under the trademark Orabronze from William H. Rohr Canada, Ltd. of Bramela, Ontario. At present, beta carotene is the preferred carotene for use in the invention, with canthaxanthin being less desirable than β carotene but preferred over α carotene.

Previously, applicants observed that the addition of an effective amount of certain solubilizing agents will solubilize beta carotene in water and water-based media, and that the solubilized β carotene does not produce undesirable color changes or grainy textures when incorporated into hydrophilic skin creams. The solubilizing agents presently used for solubilizing β carotene are cyclodextrin compounds (especially β cyclodextrins), with or without the addition of methylene chloride, 1,2-dimethoxyethane, tetrahydrofuran, and combinations of these agents.

In the case of cyclodextrins, it is found to be highly preferable to combine the β-carotene with the cyclodextrin prior to mixing it in a skin cream base. With the other solubilizers, the order of addition is less important.

Tetrahydrofuran is used in an amount of about 0.25% to 1.0% by weight of the amount of water in the final cream; it is available from Aldrich Chemical Co., Milwaukee, Wis. It has been shown to solubilize carotenoids for dispersion in aqueous solution and to thereby provide enhanced cellular uptake of same (J. S. Bertram, A. Pung, M. Churley, J. Kappock IV, L. Wilkins and R. V. Cooney, "Diverse carotenoids protect against chemically induced neoplastic transformation", *Carcinogenesis* 11: 671–678, 1991).

DME (1,2-dimethoxyethane) is also used in an amount of about 0.5% to 1% by volume of the water present in the skin cream. It is available from Fischer Scientific, Pittsburgh, Pa.

In another embodiment, the cyclodextrin-complexed carotenoid is combined with one or more additional anti-oxidants in a topical preparation. These may include cysteine, Vitamin E (tocopherol); glutathione (preferably glutathione esters) or a related thiol anti-oxidant compound in an amount of about 0.5 percent to about 3.0 percent by weight of the topical composition; SULINDAC (cis-5-fluoro-2-methyl-1-[p-(methyl-sulfinyl)benzylidene]indene-3-acetic acid), also known as CLINORIL) in an amount of generally between about 0.5% and about 1.0% by weight of the cream, but not exceeding 4 milligrams per milliliter; and enzymatic antioxidants such as superoxide dismutase. Preferably, the total quantity of the foregoing antioxidants (not including the carotenoid in the composition) is at least about 1 percent by weight, and preferably from 4 percent up to about 10.0 percent by weight.

The term vitamin E as used herein includes vitamin E from natural sources as well as pure alpha tocopherol, alpha tocopherol alkanoates in which the alkanoate has from one to five carbon atoms, and alpha tocopherol acid malonate, succinate, glutamate, and tocopheramine wherein the phenolic hydroxyl group is replaced by a primary amine. The dextrorotary compound of vitamin E alpha tocopherol is preferred. A 50 percent dry powder of dl-alpha tocopherol acetate is available from Hoffman LaRoche, Inc. of Nutley, N.J. and other sources. Liquid forms of vitamin E, which are preferred for use in manufacturing the present compositions, are available from Nature Made Nutritional Products of Los Angeles, Calif.

Glutathione is a tripeptide composed of glutamic acid, cysteine and glycine, having the formula:

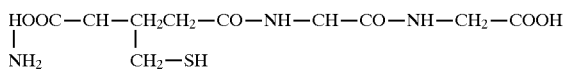

It is widely distributed in plant and animal tissue and is known to have an important role in regulating tissue oxidation. Glutathione, when present in a tissue, may act as a repetitive antioxidant provided that intermediate reduction occurs. Internally-ingested glutathione may not reach the skin areas, but inclusion of glutathione in the skin cream of this invention ensures its presence in the skin at any area of skin cream application. Additionally, the inclusion of glutathione may promote transport of the cream ingredients through the stratum corneum. The stratum corneum is a horny outer layer of human skin, which comprises essentially dead tissue and protects the epidermis. While the protective features of the stratum corneum are beneficial, it can present a barrier to topical medicaments; glutathione may thus enhance the effectiveness of the cream by helping the active ingredients penetrate this barrier.

Glutathione is available from Sigma Chemical Co. of St. Louis, Mo. Glutathione esters are highly preferred in the present invention, as these have been shown to interfere with replication of certain cancer-causing retroviruses, including the AIDS virus.

Other polypeptides which are strong antioxidants and which contain glutamic acid, cysteine, or glycine residues may be useful as partial or total substitutes for glutathione.

Superoxide dismutase (SOD) is an enzymatic antioxidant which is known to reacts with superoxide radicals to convert them into hydrogen peroxide. The hydrogen peroxide can then be acted on by another antioxidant or a second enzyme, catalase, and thus converted to a non-oxidizing form. Superoxide dismutase is available in crystalline form from Sigma Chemical, St. Louis, Mo.

SULINDAC, also known as CLINORIL, (trademarks for cis-5-fluoro-2-methyl-1-[p-(methyl-sulfinyl)- benzylidene] indene-3-acetic acid), is a nonsteroidal anti-inflammatory agent often used to treat arthritis. It has been recently found that Sulindac also can cause regression of colon polyps in humans and inhibits growth of colon tumors in animals (S. A. Skinner, A. G. Penney, and P. E. O'Brien, "Sulindac inhibits the rate of growth and appearance of colon tumors in the rat", *Arch. Surg.* 26:1094–1096, 1991); W. G. Friend, "Sulindac suppression of colorectal polyps in Gardner's syndrome", *AFP* 41:891–894, March 1990.

A number of different emollients or carriers may be used with the vitamins and other active ingredients to form an effective skin cream. These may include many ingredients common in commercial skin creams. In many skin creams, a significant amount of water is included to assist in moisturizing the skin. Generally the water is deionized or distilled water. Other ingredients which may be utilized in skin cream as a carrier for the above-identified antioxidants are glycerin, glycerol, gelatin, stearic acid, sorbitol, cetyl alcohol, parabens, various oils such as soybean oil, sunflower oil, peanut oil, wheat germ oil, sesame oil, collagen, lanolin, aloe vera extract, and similar ingredients. Petroleum jelly may also be utilized in various quantities in a skin cream or ointment of the instant invention.

An alternate skin cream like that of the instant invention may be prepared by admixing appropriate amounts of solubilized β carotene and vitamin E in a mixture of stearic acid and an oil. Stearic acid may be present anywhere from about five to 15 percent of the skin cream. Also, oils such as wheat germ oil, sesame oil, sunflower oil, rice bran oil, soybean oil, peanut oil, collagen or the like may also be admixed with stearic acid in amounts of about five to thirty-five percent.

In the embodiment including glutathione, glutathione esters, etc., the glutathione compound may be admixed in glycerin and water and added to the cream. Glutathione and glycerine are both water soluble compounds and water, as indicated above, is typically present in significant quantities, for example, from about 15 to about 50 percent of the skin cream. Glycerin may be present in quantities of from five to fifteen percent of the skin cream. Any other ingredients soluble in water desired to be used such as sodium carbonate, sodium borate, or the like which may be present in amounts generally less than about one percent by weight and aloe vera extracts, herbal extracts, perfumes, citric acid and the like in amounts up to five percent by weight may be solubilized in the water solution of glutathione.

A method for producing a decolorized aqueous solution of a carotenoid is as follows, with β carotene selected as the example. Twenty milligrams of β carotene is mixed with eighty milligrams (abbreviated "mg" hereinafter) of β cyclodextrin. The mixture is then added to 0.5 milliliters (hereinafter abbreviated "ml") of a buffered saline solution, and thoroughly mixed. The solution from this step is then added to 100 ml of distilled water, to achieve a clear solution with no visible precipitate. If a lesser amount, or no cyclodextrin is added in the first step, a red-brown precipitate is observed.

A skin cream including β carotene in an amount of about 0.1 to 0.2 percent by weight may be prepared by mixing 20 mg of β carotene with eighty mg of a cyclodextrin and 0.5 ml of a buffered saline solution. The resulting mixture, having a total volume of about 0.5 ml, can be homogenized with about 9.5 grams of a substantially white skin cream base to produce a cream which is tan or beige and smooth in texture, containing about 0.2% by weight of β carotene.

EXAMPLE 11

Mixing hydrophobic drugs together before adding β cyclodextrin.

50 milligrams of β carotene were added to 50 milligrams of vitamin E (as DL-alpha tocopherol acid succinate). To this mixture were added 50 milligrams of β cyclodextrin and 50 milligrams of gelatin derived from bovine skin (bloom 225, type III). The color of the mixture was dark brown-red, the texture was coarse and sandy. Next, 1 milliliter of D20 and 1 milliliter of glycerine were added, in that order. The color remained dark brown-red, the texture was watery. Addition of another 1 milliter of glycerine, followed by another 50 milligrams of gelatin, altered the texture of the mixture to a somewhat watery-creamy texture, but the color remained unchanged. The composition so prepared felt oily on the skin and contained small but visible particles of Vitamin E, and β carotene particles suspended in solution.

The mixture #1 was then added to 1 milliter of a commercial skin cream, LUBRIDERM, which contains water, mineral oil, petrolatum, sorbitol, lanolin, lanolin alcohol, triethanolamine, cetyl alcohol, butylparaben, methylparaben, propylparaben, and sodium chloride, in order of descending amount. The result was a somewhat gritty, red-brown cream with a pleasant smell.

EXAMPLE 12

Mixing β carotene with cyclodextrin before addition of cream base and vitamin E.

50 milligrams of β carotene were mixed thoroughly with 50 milligrams of β cyclodextrin. One milliliter of distilled $H_2O$ (d-$H_2O$) was added to the mixture of carotene and cyclodextrin. The resulting composition had a light brown color and a watery texture. Fifty milligrams of Vitamin E succinate (crystalline) were then added. The color and texture of the mixture were unchanged. Undissolved particles of Vitamin E were observed in the composition, and smaller β carotene particles were in suspension. Next, 1 milliliter of glycerine was added, followed by 150 milligrams of gelatin. These additions resulted in a composition with a light brown color and a somewhat thicker texture. The same skin cream base was added to composition 2 as in example 1, in the same amount. The resulting cream was considerably smoother than that produced by the procedure in Example 1, with no grittiness; the color was a light tan, and the cream had a pleasant smell.

EXAMPLE 13.

β Carotene and Vitamin E each separately mixed in cyclodextrin.

Fifty milligrams of β carotene were added to 100 milligrams of β cyclodextrin and 1 milliliter of d-$H_2O$. The β carotene was in a suspension, the color of the mixture was light brown, and the texture watery. Fifty microliters of dimethylsulfoxide (DMSO) were added (5 percent by volume), which slightly increased the solubilization β carotene (fewer suspended particles observed). Addition of 1% by volume of 1,2-dimethoxyethane further increased the solubilization of the β carotene, changing the color from red-brown to a light brown-yellow. The texture remained somewhat watery. Fifty milligrams of Vitamin E succinate (crystalline form) were then added, which lightened the mixture to a lighter tan color and did not change the texture. Some suspended particles of Vitamin E were observed. One milliliter of light mineral oil further increased the solubilization of both the β carotene and the vitamin E. The color of the composition was yellow-tan and the texture watery. Glycerine (1 milliliter) and/or gelatin (50 mg) were added to the mixture, followed by 1 milliliter of LUBRIDERM brand skin cream. (LUBRIDERM has the following ingredients in order of amount: water, mineral oil, petrolatum, sorbitol, lanolin, lanolin alcohol, triethanolamine, cetyl alcohol, butylparaben, methylparaben, propylparaben, sodium chloride.) The result was a cream with a white color, a very smooth texture, and pleasant smell.

From the foregoing examples it is readily seen that it is highly preferable to solubilize the β carotene by combining it with the cyclodextrin, prior to mixing with the other ingredients such as glycerine, mineral oil, or skin cream base. It is further preferable to solubilize the vitamin E succinate prior to mixing with other ingredients.

From Table V, it can be seen that mixing the β carotene with the βCD significantly increases its solubility in the LUBRIDERM skin cream. Table VI demonstrates a similar effect upon Vitamin E succinate. Inclusion of DMSO enhanced the solubilization of both active ingredients somewhat. However, it is also evident that DME (1,2-dimethoxyethane) effected the best solubilization of β carotene.

EXAMPLE 14

Spectroscopic measurements of suspensions containing β carotene, with or without cyclodextrin.

Aqueous solutions/suspensions were prepared containing selected typical cream ingredients, together with either uncomplexed or cyclodextrin-complexed β carotene. Sample A was prepared by combining 50 mg of β-carotene with 50 mg of β-cyclodextrin, and dissolving this in 1 milliliter of distilled water containing 10 mg of bovine gelatin and 0.2 ml of Dow Corning 550 silicone fluid. Sample B was prepared by taking a similar mixture of 1 ml distilled water with 10 mg bovine gelatin and 0.2 ml silicone fluid, and adding 50 mg of β carotene. The final concentration of β carotene in both samples was about 1.0% w/v. Both samples were agitated over a period of time to dissolve and mix the ingredients, until no further improvement was observable (about an hour).

TABLE V

Comparative solubility in skin cream of β carotene with different solubilization mixtures

| | Solvent #1 | | | | |
|---|---|---|---|---|---|
| Solvent #2 | βCD[1] | Gelatin | Mineral Oil | Glycerin | $H_2O$ |
| $H_2O$ | 7–8 | 2 | 3 | 3 | 1 |
| $H_2O$ + DMSO[2] | 8 | 3 | 4 | 4 | 2 |
| $H_2O$ + DMSO + EtOH (100%) | 7–8 | 3 | 4 | 4 | 2 |
| DME[3] | 8–9 | 9 | 9 | 9 | 9 |

The relative scale used was from 1 = completely nonsoluble, precipitate formed, to 10 = completely soluble, no precipitate or suspension visible. In all cases the carotene was mixed with Solvent #1 prior to mixing with Solvent #2. This mixture was in turn combined with LUBRIDERM skin cream, and the results scored.
1 = β cyclodextrin
2 = Dimethylsulfoxide
3 = 1,2 Dimethoxyethane

TABLE VI

Comparative solubility in skin cream of Vitamin E succinate with different solubilization mixtures

| | Solvent #1 | | | | |
|---|---|---|---|---|---|
| Solvent #2 | βCD[1] | Gelatin | Mineral Oil | Glycerin | $H_2O$ |
| $H_2O$ | 6–7 | 3 | 4 | 3 | 1 |
| $H_2O$ + DMSO | 7 | 4 | 5 | 4 | 2 |
| $H_2O$ + DMSO + EtOH | 7–8 | 5 | 5–6 | 5 | 2–3 |
| DME | 7–8 | 8 | 8–9 | 8 | 8 |

Relative scale and superscripts as for Table IV.

Spectroscopic measurements were then made of both of the suspensions A and B. The results are shown in Table VII and in FIG. 1. It can be seen that Sample A containing β carotene mixed with β cyclodextrin, absorbed significantly more light in the yellow-to-red wavelength region than Sample B containing no β cyclodextrin. The greater absorbance of these wavelengths by Sample A implies a reduced reflection of said wavelengths, which is consistent with a visual appearance of a reduced intensity of red to orange color as compared to Sample B. In addition, visual observation showed Sample A to be tan to yellow, whereas Sample B was red-brown.

TABLE VII

Absorbance readings* for samples A & B at five wavelengths

| | Wavelength λ (nm) | | | | |
|---|---|---|---|---|---|
| Sample | 490 | 570 | 640 | 650 | 700 |
| A. | 123 | 56.2 | 30.4 | 54.0 | 51.0 |
| B. | 197 | 45.4 | 17.5 | 29.9 | 29.2 |

*Absorbance values given as % Absorbance.

EXAMPLE 15

Addition of Cysteine to Beta-Carotene/Alpha-Cyclodextrin Complexes

An aqueous solution containing a 1:1 molar ratio of beta-carotene and alpha cyclodextrin was prepared using the identical methods as described in Example 10 except that cysteine was also added to the beta-carotene and alpha cyclodextrin solution. As further described below, various amounts of cysteine were used. Spectroscopic measurements were then made of Samples C, D, E, F (Table VIII), and of a sample consisting of uncomplexed beta-carotene, which was used as a control group. The results, as well as the amounts of cysteine added, are shown in Table VIII.

TABLE VIII

| Sample | Cysteine (equiv.)[1] | % Abs. Loss (at 450 nm)[2] |
|---|---|---|
| C | 0.0 | 45 |
| D | 0.5 | 41 |
| E | 1.0 | 39 |
| F | 2.0 | 34 |
| Control[3] | N/A | 42 |

[1]Molar equivalents relative to beta-carotene
[2]After 21 days at ambient conditions; absorbance at 450 nm monitored by UV-Vis spectrophotometer
[3]Uncomplexed beta carotene was used as the control The results were measured as percent of absorbance loss at 450 nm. The percent of absorbance loss measures the intensity of absorbance. In turn, intensity of absorbance is directly correlated to oxidation and decomposition of beta-carotene. As shown in Table VIII, the percent of absorbance loss decreases as the cysteine/beta-carotene ratio increases. The decrease in percent absorbance loss implies a reduction in oxidation of beta-carotene as a result of the antioxidative effect of cysteine.

EXAMPLE 16

Color Characteristics of Creams Containing Beta-Carotene, Cysteine and Alpha-Cyclodextrin Formulated Under a Single-Step Process Lotions containing alpha-cyclodextrin, beta-carotene, and cysteine were prepared using a single-step process. Unlike the process in Example 10, the process was effectively carried out without formation of a precursor carotenoid-cyclodextrin complex. Fifty grams of LUBRIDERM lotion were dispensed into a 250 ml WARING blender sample cup. Various quantities of alpha-cyclodextrin and cysteine (see Table IX) were added into the lotion. The lotion was then blended at a low setting (e.g. variac setting of 35 on a WARING blender) for 2 minutes. 2.75 grams of beta-carotene were added to the lotion. The lotion was blended on low for 30 minutes.

TABLE IX

| Sample # | Alpha-CD g | Cysteine[1] | Cysteine g |
|---|---|---|---|
| 1 | 0 | 0 | 0 |
| 2 | 5 | 1.0 | 1.25 |
| 3 | 5 | 2.0 | 2.50 |
| 4[2] | 5 | 0 | 0 |
| 5[2] | 0 | 2.0 | 2.50 |
| 6[3] | 0 | 0 | 0 |
| 7[3] | 5 | 0 | 0 |
| 8[3] | 5 | 2.0 | 1.25 |

[1]Molar equivalents of cysteine relative to beta-carotene.
[2]Performed under identical conditions as samples 1–3. A freshly opened can of beta-carotene was used for samples 1–3. Two days later the same can was used for samples 4–8. Beta-carotene was stored in the freezer when not in use.
[3]Samples were kept under a bed of nitrogen during formulation.

The color of the resulting lotions were then compared. The COLOR-AID, PANTONE, and COLORCURVE systems were used to characterize the observed color changes and to provide a comparison with the results obtained for the α-cyclodextrin/β-carotene complex shown in Tables I, II, and III. The results were consistent with those obtained in the above-stated Tables.

It will be recognized that various modifications and substitutions may be made in the compositions as described herein, especially to the topical carrier, without departing from the concept and scope of the invention. It should also be apparent that the teaching of the decolorization of β carotene via complexing with a cyclodextrin would be easily extended to other carotenoid compounds in which the chromophore is similar to that of β carotene. It should further be recognized that the teaching of decolorization of β carotene via mixing with a cyclodextrin and an antioxidant in a single-step process would be easily extended to other antioxidants such as glutamic acid, glycine, alpha tocopherol, retinol, or any other compounds with similar antioxidative properties.

What is claimed is:

1. A method of making a topical composition containing β carotene and having a cosmetically acceptable color, comprising the steps of:

providing an aqueous solution of a cyclodextrin compound selected from the group consisting of: α cyclodextrins, β cyclodextrins, and modified, water-soluble α or β cyclodextrins;

providing a topical carrier selected from the group consisting of pastes and creams containing both water and lipid components;

combining the cyclodextrin solution with the topical carrier in amounts to produce a molar ratio of antioxidant to cyclodextrin of from about 1:0.3 up to about 1:10;

providing an additional antioxidant compound;

combining the antioxidant solution with the topical carrier in amounts to produce a molar ratio of antioxidant to cyclodextrin of from about 1:0.3 up to about 1:10;

providing a solution of β carotene in an organic solvent; and combining said β carotene solution with the topical carrier in an amount of at least 0.5% by weight to produce a composition having a reduced color intensity in comparison to β-carotene alone in said carrier.

2. The method of claim 1, wherein said organic solvent is selected from the group consisting of: 1,2-dimethoxyethane, dimethylsulfoxide, methylene dichloride, and tetrahydrofuran.

3. The method of claim 1, wherein the topical carrier is selected from the group consisting of moisturizing skin creams and toothpastes.

4. The method of claim 1, wherein said additional antioxidant is cysteine.

5. The method of claim 4, wherein said cysteine and β-carotene are present in quantities to produce a topical composition having a molar ratio of cysteine to β-carotene of from about 1:0.1 up to about 1:10.

6. The method of claim 1, wherein said cyclodextrin is an α-cyclodextrin.

7. The method of claim 1, wherein said cyclodextrin is a β-cyclodextrin.

8. The method of claim 1, wherein said cyclodextrin is one having at least seven glucopyranose units.

9. The method of claim 1, wherein said β-carotene solution is present in an amount to provide β-carotene is at least 1% by weight of said topical carrier.

10. A method of making a topical composition containing β-carotene which has a cosmetically acceptable color comprising the steps of:
   providing a cyclodextrin compound selected from the group consisting of α cyclodextrins, β cyclodextrins, δ cyclodextrins and modified, water-soluble α, β or δ cyclodextrins;
   providing a topical carrier selected from the group consisting of pastes and creams having both water had lipid components;
   providing solution of β-carotene in an organic solvent whereby said β-carotene is present in an amount combined weights of said aqueous solution, said carrier and said organic solution;
   combining the cyclodextrins with said carrier, said aqueous solution of cyclodextrins being present in an amount such that the ratio of cyclodextrins to β-carotene in the said organic solution is from about 1:0.3 to about 1:10;
   combining said solution of β-carotene with said topical carrier containing said aqueous solution of cyclodextrins to produce a composition having a substantially neutral color.

11. The method of claim 10, wherein said organic solvent is 1,2-dimethoxyethane, dimethylsulfoxide, methylene chloride or tetrahydofuran.

12. The method of claim 10, wherein a solution of an antioxidant other than β-carotene is additionally provided and admixed with said carrier.

13. The method of claim 10, wherein said cyclodextrin is an δ-cyclodextrin on a modified δ-cyclodextrin.

14. The method of claim 10, wherein said cyclodextrin is β-cyclodextrin as a modified β-cyllodextrin.

15. The method of claim 10, wherein said cyclodextrins are provided in an aqueous solution.

16. The method of claim 10, wherein said cyclodextrin is one having at least seven glucopyranose units.

17. The method of claim 15, wherein said β-carotene is present in an amount which is at least about 1% of the combined weights of the aqueous solutions, carrier and organic solution.

18. The method of claim 13, wherein said antioxidant is cysteine in an amount to provide a molar ration of cystein to β-carotene of from about 1:0.1 to about 1:10.

* * * * *